(12) United States Patent
Islam

(10) Patent No.: US 10,307,142 B2
(45) Date of Patent: Jun. 4, 2019

(54) BIOPSY NEEDLE

(71) Applicant: Abul Bashar Mohammad Anwarul Islam, Amherst, NY (US)

(72) Inventor: Abul Bashar Mohammad Anwarul Islam, Amherst, NY (US)

( * ) Notice: Subject to any disclaimer, the term of this patent is extended or adjusted under 35 U.S.C. 154(b) by 186 days.

(21) Appl. No.: 15/334,901

(22) Filed: Oct. 26, 2016

(65) Prior Publication Data

US 2017/0119359 A1    May 4, 2017

Related U.S. Application Data

(60) Provisional application No. 62/247,530, filed on Oct. 28, 2015.

(51) Int. Cl.
*A61B 10/02*    (2006.01)

(52) U.S. Cl.
CPC ........ *A61B 10/0266* (2013.01); *A61B 10/025* (2013.01); *A61B 10/0233* (2013.01); *A61B 10/0275* (2013.01)

(58) Field of Classification Search
CPC combination set(s) only.
See application file for complete search history.

(56) References Cited

U.S. PATENT DOCUMENTS

| 6,086,543 | A * | 7/2000 | Anderson | A61B 10/0233 600/567 |
| 6,890,308 | B2 | 5/2005 | Islam | |
| 7,731,738 | B2 * | 6/2010 | Jackson | A61B 17/8635 606/300 |
| 7,967,605 | B2 * | 6/2011 | Goodis | A61C 5/42 433/102 |
| 9,572,551 | B2 * | 2/2017 | Fumex | A61B 10/025 |
| 2001/0041874 | A1 * | 11/2001 | Reydel | A61M 25/0043 604/266 |
| 2004/0267154 | A1 * | 12/2004 | Sutton | A61B 10/025 600/562 |
| 2008/0039864 | A1 * | 2/2008 | Feuer | A61B 17/4241 606/119 |
| 2009/0149775 | A1 * | 6/2009 | Lander | A61B 10/0266 600/567 |
| 2010/0168684 | A1 * | 7/2010 | Ryan | A61B 10/0233 604/272 |
| 2012/0035501 | A1 * | 2/2012 | Landrigan | A61B 10/025 600/567 |

(Continued)

*Primary Examiner* — Sean P Dougherty
(74) *Attorney, Agent, or Firm* — Vincent G. LoTempio; Kloss, Stenger & LoTempio; David T. Stephenson

(57) ABSTRACT

A biopsy needle consisting of a main portion, a linking portion and a front end portion wherein the main portion has a first bore of uniform circular cross-section, the front end portion has a smaller second bore of uniform circular cross-section and the linking portion has a shoulder between the first bore and the second bore. The outer surface of the linking portion is tapered. The open front end has multiple projecting teeth which serve to cut. There may also be serrations on the outer surface of both the front end portion and the linking portion. The biopsy needle has slits or holes to facilitate the expansion of the captured biopsy specimen and to inject cement for bone support. The needle assembly has a non-slip grip on multiple surfaces and pins hold components in place during rotation of the assembly.

13 Claims, 4 Drawing Sheets

(56) References Cited

U.S. PATENT DOCUMENTS

| | | | | |
|---|---|---|---|---|
| 2012/0136277 A1* | 5/2012 | Landrigan | ............ | A61B 10/025 600/566 |
| 2013/0260334 A1* | 10/2013 | Pernot | ...................... | A61C 5/50 433/81 |
| 2014/0309524 A1* | 10/2014 | Vetter | .................. | A61B 18/149 600/424 |
| 2015/0196287 A1* | 7/2015 | Hatta | ................. | A61B 10/0266 600/564 |

* cited by examiner

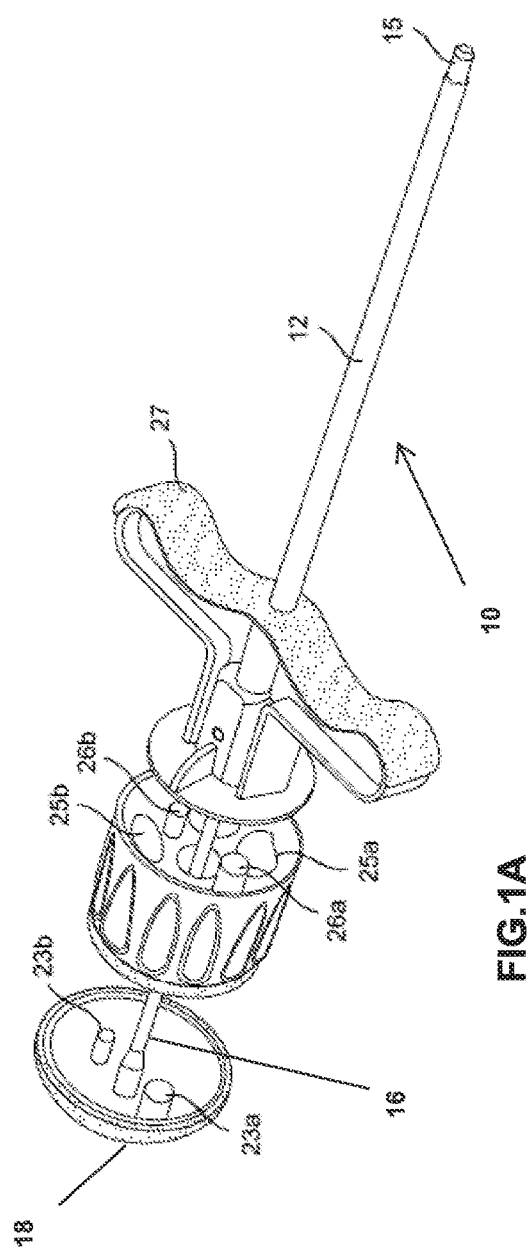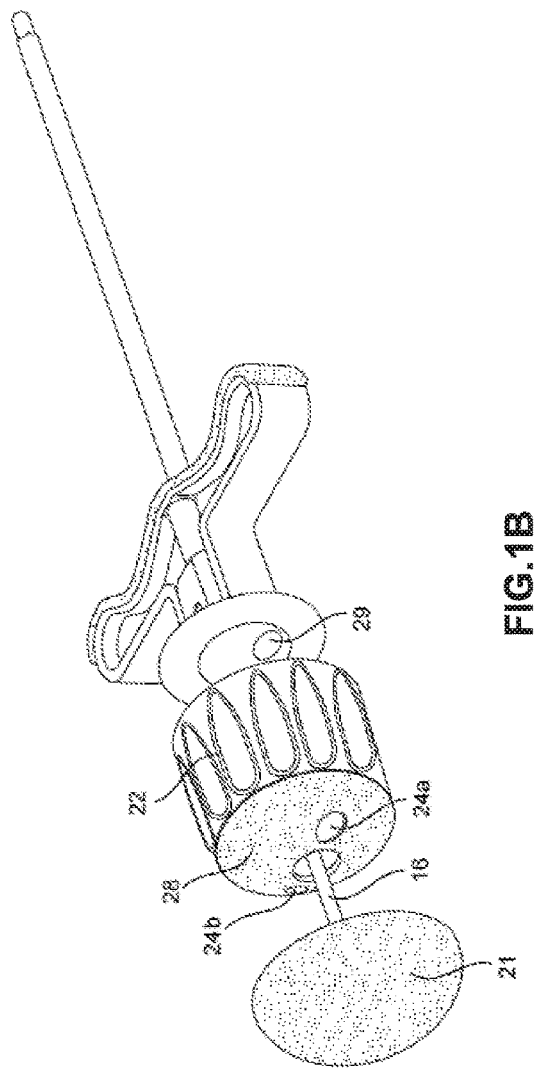

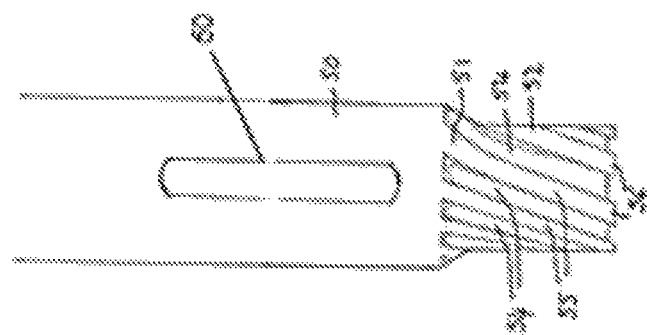

BIOPSY NEEDLE

This application claims the benefit of provisional application No. 62/247,530 having a filing date of Oct. 28, 2015.

FIELD

The present invention relates to a biopsy needle, particularly but not exclusively a biopsy needle suitable for taking a sample of bone or bone marrow with its trabeculae and marrow architecture undisturbed.

BACKGROUND

The use of a hollow metal sleeve or cannula in combination with an obturator (which may be referred to as a stilette or stylet), this combination being sometimes referred to as a trocar, is widely used in medicine for obtaining biopsy specimens. The obturator has a sharp point, and when the obturator is within the cannula, the obturator enables the combination to be inserted into the body. If the obturator is then removed, a biopsy specimen can be obtained within the cannula. U.S. Pat. No. 6,890,308 (Islam) describes a bone marrow biopsy needle of this general type, which comprises a hollow tube or hollow needle in conjunction with a trocar needle or stilette, i.e. an obturator. The hollow needle is mostly of constant internal and external diameter, but has sharp facets to form a cutting edge at its front end, and a front end portion of the hollow needle is of reduced diameter, this front end portion being formed by swaging so there is a frusto-conical transition in which the bore is tapered. If the hollow needle is pushed for example into bone marrow, without the obturator, then a sample of the marrow containing bone will go into the hollow needle; the front end portion of reduced diameter tends to grip the resulting sample, so the sample remains within the needle when the needle is withdrawn. This biopsy needle is quite effective, but an improved biopsy needle would be advantageous.

SUMMARY

According to the present invention there is provided a biopsy needle comprising an elongate hollow needle consisting of a main portion, a linking portion and a front end portion, wherein the main portion defines a first bore of uniform circular cross-section that extends along the major portion of the length of the hollow needle, the front end portion defining a second bore of uniform circular cross-section which is of smaller diameter than that of the first bore, and the linking portion linking the main portion to the front end portion; within the linking portion the internal diameter of the bore decreases from the main portion to the front end portion, defining a shoulder within the bore; and the front end portion having an open front end provided with a cutting formation; wherein the outer surface of the front end portion is generally cylindrical and of uniform diameter, while the outer surface of the linking portion is of tapering shape; and wherein the open front end defines multiple projecting teeth to define the cutting formation. The projecting teeth may be of the same radial thickness as the front end portion from which they project, so they are quite strong and not readily damaged in use.

In one embodiment the outer surface of the front end portion and of the linking portion defines multiple sharp-edged parallel serrations whose sharp edges extend in a direction with a component parallel to the longitudinal axis of the needle. For example, they may extend in a direction that is parallel to the longitudinal axis of the needle.

The present invention relates to a biopsy needle, particularly but not exclusively a biopsy needle suitable for taking a sample of bone or bone marrow with its trabeculae and marrow architecture undisturbed.

The linking portion may have a bore that varies linearly, and hence the outer surface of the linking portion may taper linearly so as to define a frusto-conical surface. The multiple projecting teeth may be shaped like saw teeth.

The outside diameter of the main portion of the hollow needle typically depends on its application, as for example a pediatric needle may be of external diameter about 2.4 mm, a standard needle may be of external diameter about 3.3 mm, and an orthopedic needle may be of diameter about 4.0 mm. The diameter of the bore obviously depends upon the wall thickness which may for example be between 0.3 mm and 0.5 mm. It is advantageous to obtain as large a diameter sample as is feasible with a given external diameter of the hollow needle. The radial height of the shoulder is at least 0.1 mm, but preferably no greater than 0.5 mm, for example 0.2 mm or 0.3 mm. It is desirable if the second bore is of diameter at least 70% that of the first bore, for example at least 80%. The axial length of the second bore in the front end portion is preferably at least 2 mm, but preferably no longer than 5 mm.

In use the biopsy specimen passes through the second bore, in the front end portion, and into the first bore, in the main portion. As it passes beyond the shoulder provided by the linking portion, it tends to expand radially as it is no longer constrained by the second bore. When the biopsy needle is withdrawn, the specimen is held partly by this shoulder, and partly by the length of the specimen that is within the second bore.

The present invention relates to a biopsy needle, particularly but not exclusively a biopsy needle suitable for taking a sample of bone or bone marrow with its trabeculae and marrow architecture undisturbed.

The serrations may for example be of triangular cross-sectional shape. They extend over the entire surface of the front end portion and of the linking portion.

BRIEF DESCRIPTION OF THE DRAWINGS

The invention will now be further and more particularly described, by way of example only, and with reference to the accompanying drawings in which:

FIGS. 1A and 1B show perspective views of components of a biopsy needle assembly of the invention;

FIGS. 5A and 5B show a side view of the front end of an alternative modification to the biopsy needle of FIG. 2 having slits.

DETAILED DESCRIPTION

Figure 2:
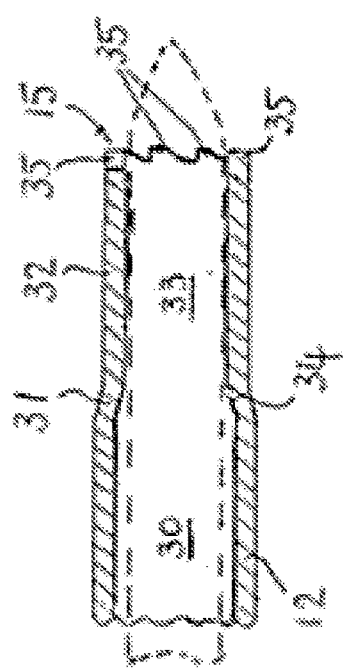
FIG. 2 shows a longitudinal sectional view of the front end of the biopsy needle when assembled, the obturator being shown in broken lines.

Referring now to FIG. 1, a biopsy needle 10 consists of three components, which assemble to form a trocar. There is a hollow needle 12, which in this embodiment is provided with a molded plastic T-bar handle 27 at the proximal end, and has a cutting formation 15 at its front end; there is a stylet 16 (which may be referred to as a trocar needle), which has a molded plastic domed head 18 at one end, and a sharp pointed tip 20 (shown in FIG. 5A) at the other end; and there is a molded plastic spacer 22.

The spacer 22 defines a through-hole which widens out at each end; the stylet 16 can pass through this through-hole, and the spacer 22 is used to ensure the stylet 16 is aligned with the bore of the hollow needle 12 during insertion. For use of the biopsy needle 10 to obtain a sample from a patient, the spacer 22 is fitted onto the proximal end of the T-bar handle 27, and the stylet 16 is then inserted through the spacer 22 and along the hollow needle 12. In this arrangement the tip 20 of the stylet 16 projects beyond the cutting formation 15 at the front end of the hollow needle 12. The details of the cutting formation 15 are not shown in FIG. 1.

The front face of the trocar head 18 defines two projecting pins 23a and 23b which engage in corresponding recesses 24a and 24b (shown in FIG. 1B) on the rear face of the plastic spacer 22, and the front face of the plastic spacer 22 defines two projecting pins 26a and 26b, adjacent hollow portions 25a and 25b, which engage in corresponding recesses 29 on the rear face of the T-bar handle 27. Hence the stylet 16 is held in a fixed orientation relative to the hollow needle 12, and the hollow needle 12 and the stylet 16 rotate together if the T-bar handle 27 is turned. The projecting pins, such as 23a and 23b, may be of different diameters which correspond to recesses, such as 24a and 24b, which are of different diameters, to direct the orientation of the stilette.

Referring now to FIG. 2, this shows the front end of the hollow needle 12 in more detail. The hollow needle 12 is of uniform external diameter along the bulk of its length, with a uniform bore 30, but the front end is swaged down so as to form a tapering linking portion 31 and a front end portion 32. The front end portion 32 defines a second bore 33 of uniform circular cross-section which is of smaller diameter than the bore 30 of the remainder of the hollow needle 12, so the linking portion 31 forms a shoulder 34 within the bore. In one embodiment the internal diameter of the bore 30 is 2.5 mm, while the internal diameter of the second bore 33 is 2.1 mm; and the front end portion 32 is of length 4.0 mm. The front end portion 32 defines a cutting formation 15 around the open end of the hollow needle 12. In this embodiment the cutting formation 15 is defined by several asymmetrical saw teeth 35; there may for example be seven teeth 35 around the circumference of the open end, or in another embodiment there may be five such teeth 35.

The biopsy needle 10 can be used to obtain a sample of bone marrow, that is to say a core sample in which marrow and its associated bony trabeculae are substantially undisturbed, or to obtain a core sample of bone, from a patient. The biopsy needle 10 is first assembled using the stylet 16 inside the hollow needle 12, with the spacer 22 between the T-bar handle 27 and the domed head 18, so that the sharp pointed tip 20 projects beyond the cutting formation 15, as indicated in broken lines in FIG. 2; this assembly acts as a trocar. Where a sample of bone marrow is to be obtained, this is usually performed on the right or left posterior iliac crests. After making an incision in the patient's skin under local anesthetic, the biopsy needle 10 is inserted through the incision and gradually advanced with clockwise and anti-clockwise twisting of the handle 27 while pointing towards the bone. Once the cortex of the posterior ilium has been penetrated, the stylet 16 is withdrawn from the biopsy needle 10. The hollow needle 12 is then gradually pushed forward into the bone marrow, typically with clockwise and counter-clockwise rotary twisting of the handle 27, until the desired depth (for example 20 mm) has been reached. At this point bone marrow will have been forced 20 mm through the bore 33 into the wider bore 30. The hollow needle 12 may then be rotated about its longitudinal axis sufficiently to ensure that all the trabecular connections at the base of the specimen within the bore 33 have been completely severed. The hollow needle 12 can then be withdrawn, containing the specimen of bone marrow.

As indicated above, as the hollow needle 12 is pushed forward or advanced into the bone marrow, a biopsy specimen of bone marrow with trabeculae is forced through the bore 33 into the wider bore 30. As it enters the wider bore 30 it tends to expand, as the trabeculae are no longer constrained by the wall of the bore 33; whereas the portion within the bore 33 is somewhat compressed. The length of the bore 33, in combination with the shoulder 34, ensures that the biopsy specimen remains securely held within the hollow needle 12 when the hollow needle 12 is withdrawn from the patient.

After the hollow needle 12 has been used to obtain a biopsy specimen, the through-hole of the plastic spacer 22 can be fitted onto the front end of the hollow needle 12, and the stylet 16 can then be pushed through the through-hole and so through the front end of the hollow needle 12, so as to remove the biopsy specimen. The biopsy specimen is pushed entirely into the bore 30, and removed through the proximal end of the hollow needle 12.

Although this has been described in the context of obtaining a bone marrow biopsy specimen, substantially the same process may be used to obtain a sample of bone. The cutting formation 15 formed by the set of teeth 35 ensures that the hollow needle 12 can cut a cylindrical specimen from the bone.

Figure 3:
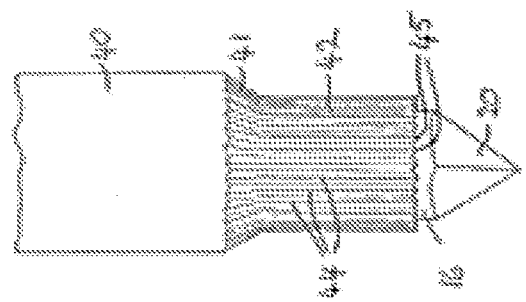
FIG. 3 shows a side view of the front end of a modification to the biopsy needle of FIG. 2.

In some applications it has been found that a bone may be hard, and so difficult to penetrate. Referring now to FIG. 3 there is shown an alternative hollow needle 40 which is a modification to the hollow needle 12, features that are the same being referred to by the same reference numerals. In FIG. 3 the pointed tip 20 of the stylet 16 is shown protruding from the open end of the hollow needle 40. The open end of the hollow needle 40 is swaged down so that the bore is substantially the same as described in relation to FIG. 2, with a second bore 33 of uniform diameter, a shoulder 34, and a bore 30 along the rest of the length of the hollow needle 40 (the features of the bore not being visible in FIG. 3). The outer surface similarly defines a front end portion 42 and a short frusto-conical linking portion 41, but in this case there are multiple parallel serrations 44 on the outer surface of the front end portion 42 and the linking portion 41. Each serration 44 is of triangular cross-section, and the serrations 44 align with projecting triangular teeth 45 around the open end of the hollow needle 40.

Figure 4:
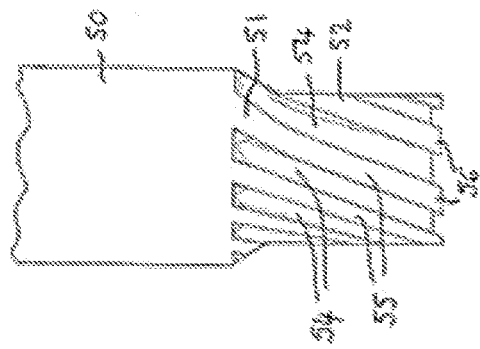
FIG. 4 shows a side view of the front end of an alternative modification to the biopsy needle of FIG. 2.

Referring now to FIG. 4 there is shown another alternative hollow needle 50 which is a modification to the hollow needle 12, features that are the same being referred to by the same reference numerals. The stylet 16 is not shown in this figure. The open end of the hollow needle 50 is swaged down so that the bore is substantially as described in relation to FIG. 2, with a second bore 33 of uniform diameter, a shoulder 34, and bore 30 along the rest of the length of the hollow needle 50 (the features of the bore not being visible in FIG. 4). The outer surface similarly defines a front end portion 52 and a short frusto-conical linking portion 51, but in this case there are multiple rectangular grooves 54 on the outer surface of the front end portion 52 and the linking portion 51. The grooves 54 extend along parts of parallel helical paths, that is to say a path at an angle to the longitudinal axis of the hollow needle 50, so there are helical sharp-edged ridges 55 between successive grooves 54. The ridges 55 have the effect that the hollow needle 50 acts like a drill bit when rotated. In addition, each ridge 55 extends at the open end slightly beyond the end of the adjacent rectangular grooves 54, to define a saw tooth 56.

In all three embodiments, the projecting teeth 35, 45 and 56 are of the same radial thickness as the front end portion 32, 42, 52 from which they project, so they are quite strong and not readily damaged in use. The hollow needles 40 and 50 are very effective at penetrating hard cortical bone, both because of the strong projecting teeth 45 and 56 and because of the abrading and cutting effect of the serrations 44 or of the sharp-edged ridges 55. In other respects the hollow needles 40 and 50 operated in substantially the same way as described above, as they are effective at securing a biopsy sample for the reasons explained above.

Shown in FIGS. 5A and 5B is an alternative embodiment having a needle with slits 60. The distal end of this needle has at least two longitudinal slits 60 on opposite sides of the needle. These slits facilitate the expansion of the captured biopsy specimen once it has passed through the open circular end of the needle, particularly in needles of uniform diameter throughout and without a narrower distal portion linking to a wider proximal portion, and thereby help to retain it in the lumen of the needle. The two slits, in one embodiment, are 15 mm long and 1.5 mm wide and are on opposite sides near the distal cutting end of the needle. The slits facilitate the relative expansion of the core biopsy once it has passed beyond the fixed circular opening at the terminus of the needle and has entered into the hollow shaft. The slits may be included with any of the various embodiments of needles disclosed herein. The slits can be one long one on either side or three or more circumferentially. Similarly the slits 60 can be broken down to two three on either side or more circumferentially. The width of each slit can vary from 1-2 mm and the length may vary from 5-10 mm each when the number of slit is two or it may vary from 3-5 mm each when the number of slits is three.

In an alternative embodiment of the present disclosure, the needle may be used to introduce cement to a fractured bone through side holes, or alternatively slits 60, in the needle. Conventionally, a mixture of cement (methylmethacrylate) mixed with barium is injected into a fractured vertebral body via a needle. Sometimes the injection of cement is preceded by introduction of a balloon to form a recess so that an adequate amount of cement can be introduced (balloon kyphoplasty). Occasionally a biopsy is taken from the damaged vertebral body prior to the injection. This is usually done with standard, non-specialized needles. Unfortunately such needles are apt to provide either unsatisfactory samples or no biopsies at all as they do not have a core retention/capturing device. The biopsy often slips out of the needle even when a negative pressure is applied by attaching a syringe.

Figure 6B:
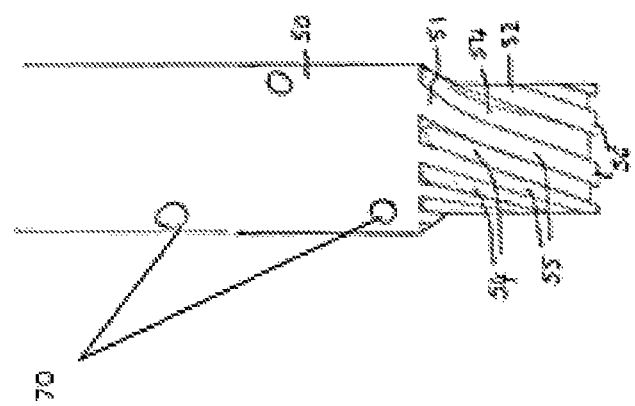
FIGS. 6A and 6B show a side view of the front end of an alternative modification to the biopsy needle of FIG. 2 having side holes.
Figure 6A:
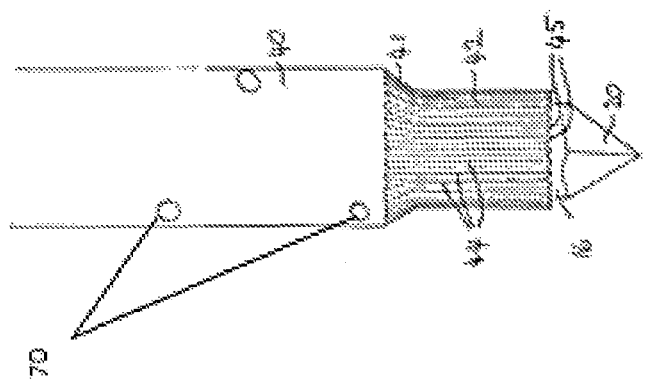

Shown in FIGS. 6A and 6B is an alternative embodiment having side holes 70. The side holes 70, and also the slits 60 shown in FIGS. 5A and 5B, may facilitate cement being injected with a syringe attached to the proximal end of the needle. During this procedure the needle can be rotated so that the cement can be delivered uniformly to fill the cavity. As a result when cement is introduced through this needle it not only flows out through the distal large opening but also through the slits 60 or side holes 70 located in the pre-terminal segment of the needle. This provides a rapid and effective method of delivering the cement into the affected vertebral body. The side holes may range from 1-3 mm in diameter and may be spaced longitudinally along the needle in a spiral pattern to maintain the strength of the needle. Preferably, 3-6 side holes 70 are placed along the side of the needle.

A needle with slits 60 or side holes 70 of the present disclosure enmeshes and embraces the bony trabeculae with cement thus providing a scaffolding and additional support for the vertebra. A further advantage of this system is the fact that it reduces the need for extra instrumentation (curette and balloon) and additional steps such as introducing and curetting first and then introducing and removing the balloon. The side holes 70 may be included with any of the various embodiment s of needles described herein.

It will be appreciated that the biopsy needle 10 as described above may be modified in various ways while remaining within the scope of the invention as defined by the claims. For example, although the handles 27, trocar head 18 and spacer 22 are described as being of plastic, each one may be of another material, for example stainless steel. Furthermore it has been found that the surfaces of the handles 27, trocar head 18 and spacer 22 can be slippery. It may therefore be appropriate to provide at least part of these surfaces with a non-slip finish or non-slip surface elements. Such non-slip surface elements may for example be provided by a thermoplastic elastomer, such as a co-polyether ester; while the remaining parts of the handles 27, trocar head 18 and spacer 22 may be molded from a compatible polymer, such as thermoplastic polyester and/or polycarbonate. Shown in FIG. 1B are the trocar head non-slip surface 21 and the spacer non-slip surface 28, along with a non-slip surface on the lower portion of T-bar handle 27.

Instead of being manually operated, the distal end of the biopsy needle 10 may be connected to a motor, to be rotated continuously in one direction. For that reason, the serrations 44 may be asymmetrical in cross-section, so as to abrade the bone most effectively when turned in the direction of rotation of such a motor. Similarly the sharp-edged ridges 55 may also be asymmetrical, so as to drill through the bone most effectively when turned in the direction of rotation of such a motor.

It will be appreciated that the hollow needles and assembly are described by way of example only, and that they may be modified while remaining within the scope of the invention as defined by the claims. For example where there are serrations or ridges, they may have a different shape, and they may extend in a different direction relative to the longitudinal axis.

What is claimed is:

1. A biopsy needle comprising:
an elongate hollow needle having a main portion, a linking portion and a front end portion, wherein the main portion defines a first bore of uniform circular cross-section that extends along a major portion of a length of the hollow needle, the front end portion defining a second bore of uniform circular cross-section which is of smaller diameter than that of the first bore, and the linking portion linking the main portion to the front end portion; within the linking portion an internal diameter of a linking bore decreases from the main portion to the front end portion, defining a shoulder; and the front end portion having an open front end provided with a cutting formation; wherein an outer surface of the front end portion is generally cylindrical and of uniform diameter, while the outer surface of the linking portion is of tapering shape; and wherein the open front end defines a plurality of projecting teeth to define the cutting formation, wherein an entire outer surface of the front end portion and of the linking portion defines a plurality of grooves, wherein the plurality of grooves extend uninterrupted from a distal end of the main portion to a distal end of the front portion; wherein between the plurality of grooves are a plurality of sharp-edged ridges; wherein the plurality of grooves and the plurality of sharp-edged ridges extend along parts of parallel helical paths; wherein the plurality of sharp-edged ridges form the plurality of projecting teeth at the distal end of the front portion;

wherein a width of the plurality of projecting teeth is consistent with a width of the plurality of sharp-edged ridges, and wherein a distal edge of the plurality of projecting teeth is straight and perpendicular to a longitudinal axis of the needle; and wherein the needle has at least two circular side holes.

2. A biopsy needle of claim 1, wherein the plurality of projecting teeth may be of the same radial thickness as the front end portion from which they project.

3. The biopsy needle of claim 1, wherein the at least two circular side holes extend longitudinally at a distal end of the needle for introducing cement into a bone.

4. The biopsy needle of claim 3, wherein the at least two circular side holes extend in a spiral pattern.

5. The biopsy needle of claim 3, wherein each circular side hole has a diameter between 1 and 3 mm.

6. A biopsy needle comprising:

an elongate hollow needle having a main portion, a linking portion and a front end portion, wherein the main portion defines a first bore of uniform circular cross-section that extends along a major portion of a length of the hollow needle, the front end portion defining a second bore of uniform circular cross-section which is of smaller diameter than that of the first bore, and the linking portion linking the main portion to the front end portion; within the linking portion an internal diameter of a linking bore decreases from the main portion to the front end portion, defining a shoulder; and the front end portion having an open front end provided with a cutting formation; wherein an outer surface of the front end portion is generally cylindrical and of uniform diameter, while the outer surface of the linking portion is of tapering shape; and wherein the open front end defines a plurality of projecting teeth to define the cutting formation;

wherein an entire outer surface of the front end portion and of the linking portion defines a plurality of grooves, wherein the plurality of grooves extend uninterrupted from a distal end of the main portion to a distal end of the front portion, wherein between the plurality of grooves are a plurality of sharp-edged ridges; wherein the plurality of grooves and the plurality of sharp-edged ridges extend along parts of parallel helical paths; wherein at the distal end of the front portion the plurality of sharp-edged ridges form the plurality of projecting teeth; and wherein the needle has at least two circular side holes.

7. The biopsy needle of claim 6, wherein the least two circular side holes extend longitudinally at a distal end of the needle for introducing cement into a bone.

8. The biopsy needle of claim 7, wherein the at least two circular side holes extend in a spiral pattern.

9. The biopsy needle of claim 7, wherein each circular side hole has a diameter between 1 and 3 mm.

10. A biopsy needle comprising:

an elongate hollow needle having a main portion, a linking portion and a front end portion, wherein the main portion defines a first bore of uniform circular cross-section that extends along a major portion of a length of the hollow needle, the front end portion defining a second bore of uniform circular cross-section which is of smaller diameter than that of the first bore, and the linking portion linking the main portion to the front end portion; within the linking portion an internal diameter of a linking bore decreases from the main portion to the front end portion, defining a shoulder; and the front end portion having an open front end provided with a cutting formation; wherein an outer surface of the front end portion is generally cylindrical and of uniform diameter, while the outer surface of the linking portion is of tapering shape; and wherein the open front end defines a plurality of projecting teeth to define the cutting formation, wherein the entire outer surface of the front end portion and of the linking portion defines a plurality of grooves, wherein the plurality of grooves extend uninterrupted from a distal end of the main portion to a distal end of the front portion, wherein between the plurality of grooves are a plurality of sharp-edged ridges; wherein the plurality of sharp-edged ridges form the plurality of projecting teeth at a distal end of the front portion; and wherein the needle has at least two circular side holes.

11. The biopsy needle of claim 10, wherein the at least two circular side holes extend longitudinally at a distal end of the needle for introducing cement into a bone.

12. The biopsy needle of claim 11, wherein the at least two circular side holes extend in a spiral pattern.

13. The biopsy needle of claim 11, wherein each circular side hole has a diameter between 1 and 3 mm.

* * * * *